United States Patent
Mouthon et al.

(10) Patent No.: US 8,609,356 B2
(45) Date of Patent: Dec. 17, 2013

(54) METHOD FOR DIAGNOSING PULMONARY ARTERY HYPERTENSION

(75) Inventors: Luc Mouthon, Saint Mandé (FR); Marc Humbert, Issy les Moulineaux (FR); Mathieu Tamby, Aulnay sous Bois (FR)

(73) Assignees: Assistance Publique-Hopitaux de Paris, Paris (FR); Universite Paris Descartes, Paris Cedes (FR); Universite Paris-Sud 11, Paris Cedes (FR)

( * ) Notice: Subject to any disclaimer, the term of this patent is extended or adjusted under 35 U.S.C. 154(b) by 379 days.

(21) Appl. No.: 12/936,745

(22) PCT Filed: Apr. 10, 2009

(86) PCT No.: PCT/FR2009/050661
§ 371 (c)(1),
(2), (4) Date: Oct. 7, 2010

(87) PCT Pub. No.: WO2009/136112
PCT Pub. Date: Nov. 12, 2009

(65) Prior Publication Data
US 2011/0033876 A1 Feb. 10, 2011

(30) Foreign Application Priority Data

Apr. 11, 2008 (FR) .................................. 08 52459

(51) Int. Cl.
| | | |
|---|---|---|
| *G01N 33/53* | (2006.01) | |
| *G01N 33/535* | (2006.01) | |
| *G01N 33/543* | (2006.01) | |
| *G01N 33/564* | (2006.01) | |
| *G01N 33/566* | (2006.01) | |
| *C07K 16/18* | (2006.01) | |

(52) U.S. Cl.
USPC .......... 435/7.92; 435/7.1; 435/7.21; 435/7.95; 435/974; 436/506; 436/518; 436/536; 436/811; 530/389.1; 530/898

(58) Field of Classification Search
USPC ........ 435/7.1, 7.21, 7.92, 7.95, 974; 436/506, 436/518, 536, 811; 530/389.1, 868
See application file for complete search history.

(56) References Cited

U.S. PATENT DOCUMENTS

| | | | | |
|---|---|---|---|---|
| 4,880,750 A | * | 11/1989 | Francoeur | 436/501 |
| 6,989,276 B2 | * | 1/2006 | Thompson et al. | 436/518 |
| 2008/0026485 A1 | * | 1/2008 | Hueber et al. | 436/507 |
| 2012/0010095 A1 | * | 1/2012 | Jones et al. | 506/9 |

FOREIGN PATENT DOCUMENTS

| | | |
|---|---|---|
| WO | WO 99/43308 | 9/1999 |
| WO | WO 2005/009366 | 2/2005 |

OTHER PUBLICATIONS

Tilson, 1995. Similarities of an autoantigen in aneurysmal disease of the human abdominal aorta to a 36-kDa microfibril-associated bovine aortic glycoprotein. Biochem. Biophys. Res. Comm. 213: 40-43.*
Duneér et al., 2009. Immune responses against fibronectin modified by lipoprotein oxidation and their association with cardiovascular disease. J. Int. Med. 265: 593-603.*
Mouthon et al., 2005. Pulmonary arterial hypertension: and autoimmune disease? Eur. Resp. J. 26: 986-988.*
Nicolls et al., 2005. Autoimmunity and pulmonary hypertension: a perspective. Eur. Resp. J. 26: 1110-1118.*
Tamby et al., 2005. Anti-endothelial cell antibodies in idiopathic and systemic sclerosis associated pulmonary arterial hypertension. Thorax 60: 765-772.*
Ihida-Stansbury et al., 2006. Tenascin-C is induced by mutated BMP type II receptors in familial forms of pulmonary arterial hypertension. Am. J. Physiol. Lung Cell. Mol. Physiol. 291: L694-L702.*
Jeffrey et al., "Molecular and cellular basis pulmonary vascular remodeling in pulmonary hypertension," Progress in Cardiovascular Diseases, Sanders, Philadelphia, PA, vol. 45, No. 3, pp. 173-202 (2002) XP005128803.

* cited by examiner

*Primary Examiner* — Mark Shibuya
*Assistant Examiner* — James L Grun
(74) *Attorney, Agent, or Firm* — Cesari and McKenna, LLP

(57) ABSTRACT

The invention relates to an in vitro method for detecting pulmonary arterial hypertension (PAHT), or the risk of developing PAHT, which includes determining the presence and/or amount of anti-tenascin C antibodies in a biological sample from a patient.

10 Claims, 2 Drawing Sheets

SEQUENCE LISTING

<160> NUMBER OF SEQ ID NOS: 1

<210> SEQ ID NO 1
<211> LENGTH: 2201
<212> TYPE: PRT
<213> ORGANISM: Homo sapiens
<220> FEATURE:
<221> NAME/KEY: MISC_FEATURE
<222> LOCATION: (181)..(290)
<223> OTHER INFORMATION: antigenic fragment

<400> SEQUENCE: 1

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80

Ser Glu Pro Ser Glu Ser Phe Gln Glu His Thr Val Asp Gly Glu Asn
                85                  90                  95

Gln Ile Val Phe Thr His Arg Ile Asn Ile Pro Arg Arg Ala Cys Gly
            100                 105                 110

Cys Ala Ala Ala Pro Asp Val Lys Glu Leu Leu Ser Arg Leu Glu Glu
        115                 120                 125

Leu Glu Asn Leu Val Ser Ser Leu Arg Glu Gln Cys Thr Ala Gly Ala
    130                 135                 140

Gly Cys Cys Leu Gln Pro Ala Thr Gly Arg Leu Asp Thr Arg Pro Phe
145                 150                 155                 160

Cys Ser Gly Arg Gly Asn Phe Ser Thr Glu Gly Cys Gly Cys Val Cys
                165                 170                 175

Glu Pro Gly Trp Lys Gly Pro Asn Cys Ser Glu Pro Glu Cys Pro Gly
            180                 185                 190

Asn Cys His Leu Arg Gly Arg Cys Ile Asp Gly Gln Cys Ile Cys Asp
        195                 200                 205

Asp Gly Phe Thr Gly Glu Asp Cys Ser Gln Leu Ala Cys Pro Ser Asp
    210                 215                 220

Cys Asn Asp Gln Gly Lys Cys Val Asn Gly Val Cys Ile Cys Phe Glu
225                 230                 235                 240

Gly Tyr Ala Gly Ala Asp Cys Ser Arg Glu Ile Cys Pro Val Pro Cys
                245                 250                 255

Ser Glu Glu His Gly Thr Cys Val Asp Gly Leu Cys Val Cys His Asp
            260                 265                 270

Gly Phe Ala Gly Asp Asp Cys Asn Lys Pro Leu Cys Leu Asn Asn Cys
        275                 280                 285

Tyr Asn Arg Gly Arg Cys Val Glu Asn Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr

```
                340             345             350
Gln Gly Arg Cys Glu Glu Gly Gln Cys Val Cys Asp Glu Gly Phe Ala
            355                 360             365
Gly Leu Asp Cys Ser Glu Lys Arg Cys Pro Ala Asp Cys His Asn Arg
        370                 375             380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
        435                 440                 445
Cys Val Glu Gly Lys Cys Val Cys Glu Gln Gly Phe Lys Gly Tyr Asp
    450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
            500                 505                 510
Asp Gly Gln Cys Val Cys Glu Asp Gly Phe Thr Gly Pro Asp Cys Ala
        515                 520                 525
Glu Leu Ser Cys Pro Asn Asp Cys His Gly Gln Gly Arg Cys Val Asn
    530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
            580                 585                 590
Ser Cys Pro Ser Asp Cys Asn Asn Leu Gly Gln Cys Val Ser Gly Arg
        595                 600                 605
Cys Ile Cys Asn Glu Gly Tyr Ser Gly Glu Asp Cys Ser Glu Val Ser
    610                 615                 620
Pro Pro Lys Asp Leu Val Val Thr Glu Val Thr Glu Glu Thr Val Asn
625                 630                 635                 640
Leu Ala Trp Asp Asn Glu Met Arg Val Thr Glu Tyr Leu Val Val Tyr
                645                 650                 655
Thr Pro Thr His Glu Gly Gly Leu Glu Met Gln Phe Arg Val Pro Gly
            660                 665                 670
Asp Gln Thr Ser Thr Ile Ile Gln Glu Leu Glu Pro Gly Val Glu Tyr
        675                 680                 685
Phe Ile Arg Val Phe Ala Ile Leu Glu Asn Lys Lys Ser Ile Pro Val
    690                 695                 700
Ser Ala Arg Val Ala Thr Tyr Leu Pro Ala Pro Glu Gly Leu Lys Phe
705                 710                 715                 720
Lys Ser Ile Lys Glu Thr Ser Val Glu Val Glu Trp Asp Pro Leu Asp
                725                 730                 735
Ile Ala Phe Glu Thr Trp Glu Ile Ile Phe Arg Asn Met Asn Lys Glu
            740                 745                 750
Asp Glu Gly Glu Ile Thr Lys Ser Leu Arg Arg Pro Glu Thr Ser Tyr
        755                 760                 765
```

-continued

```
Arg Gln Thr Gly Leu Ala Pro Gly Gln Glu Tyr Glu Ile Ser Leu His
            770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
                820                 825                 830

Ile Glu Leu Thr Tyr Gly Ile Lys Asp Val Pro Gly Asp Arg Thr Thr
            835                 840                 845

Ile Asp Leu Thr Glu Asp Glu Asn Gln Tyr Ser Ile Gly Asn Leu Lys
        850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
            915                 920                 925

Pro Ile Ser Gly Gly Asp His Ala Glu Val Asp Val Pro Lys Ser Gln
        930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Gly Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
            995                 1000                1005

Leu Ala Lys Phe Asp Arg Tyr Arg Leu Asn Tyr Ser Leu Pro Thr
        1010                1015                1020

Gly Gln Trp Val Gly Val Gln Leu Pro Arg Asn Thr Thr Ser Tyr
        1025                1030                1035

Val Leu Arg Gly Leu Glu Pro Gly Gln Glu Tyr Asn Val Leu Leu
        1040                1045                1050

Thr Ala Glu Lys Gly Arg His Lys Ser Lys Pro Ala Arg Val Lys
        1055                1060                1065

Ala Ser Thr Glu Gln Ala Pro Glu Leu Glu Asn Leu Thr Val Thr
        1070                1075                1080

Glu Val Gly Trp Asp Gly Leu Arg Leu Asn Trp Thr Ala Ala Asp
        1085                1090                1095

Gln Ala Tyr Glu His Phe Ile Ile Gln Val Gln Glu Ala Asn Lys
        1100                1105                1110

Val Glu Ala Ala Arg Asn Leu Thr Val Pro Gly Ser Leu Arg Ala
        1115                1120                1125

Val Asp Ile Pro Gly Leu Lys Ala Ala Thr Pro Tyr Thr Val Ser
        1130                1135                1140

Ile Tyr Gly Val Ile Gln Gly Tyr Arg Thr Pro Val Leu Ser Ala
        1145                1150                1155

Glu Ala Ser Thr Gly Glu Thr Pro Asn Leu Gly Glu Val Val Val
        1160                1165                1170

Ala Glu Val Gly Trp Asp Ala Leu Lys Leu Asn Trp Thr Ala Pro
        1175                1180                1185
```

-continued

Glu Gly Ala Tyr Glu Tyr Phe Phe Ile Gln Val Gln Glu Ala Asp
    1190            1195                1200

Thr Val Glu Ala Ala Gln Asn Leu Thr Val Pro Gly Gly Leu Arg
    1205            1210                1215

Ser Thr Asp Leu Pro Gly Leu Lys Ala Ala Thr His Tyr Thr Ile
    1220            1225                1230

Thr Ile Arg Gly Val Thr Gln Asp Phe Ser Thr Thr Pro Leu Ser
    1235            1240                1245

Val Glu Val Leu Thr Glu Glu Val Pro Asp Met Gly Asn Leu Thr
    1250            1255                1260

Val Thr Glu Val Ser Trp Asp Ala Leu Arg Leu Asn Trp Thr Thr
    1265            1270                1275

Pro Asp Gly Thr Tyr Asp Gln Phe Thr Ile Gln Val Gln Glu Ala
    1280            1285                1290

Asp Gln Val Glu Glu Ala His Asn Leu Thr Val Pro Gly Ser Leu
    1295            1300                1305

Arg Ser Met Glu Ile Pro Gly Leu Arg Ala Gly Thr Pro Tyr Thr
    1310            1315                1320

Val Thr Leu His Gly Glu Val Arg Gly His Ser Thr Arg Pro Leu
    1325            1330                1335

Ala Val Glu Val Val Thr Glu Asp Leu Pro Gln Leu Gly Asp Leu
    1340            1345                1350

Ala Val Ser Glu Val Gly Trp Asp Gly Leu Arg Leu Asn Trp Thr
    1355            1360                1365

Ala Ala Asp Asn Ala Tyr Glu His Phe Val Ile Gln Val Gln Glu
    1370            1375                1380

Val Asn Lys Val Glu Ala Ala Gln Asn Leu Thr Leu Pro Gly Ser
    1385            1390                1395

Leu Arg Ala Val Asp Ile Pro Gly Leu Glu Ala Ala Thr Pro Tyr
    1400            1405                1410

Arg Val Ser Ile Tyr Gly Val Ile Arg Gly Tyr Arg Thr Pro Val
    1415            1420                1425

Leu Ser Ala Glu Ala Ser Thr Ala Lys Glu Pro Glu Ile Gly Asn
    1430            1435                1440

Leu Asn Val Ser Asp Ile Thr Pro Glu Ser Phe Asn Leu Ser Trp
    1445            1450                1455

Met Ala Thr Asp Gly Ile Phe Glu Thr Phe Thr Ile Glu Ile Ile
    1460            1465                1470

Asp Ser Asn Arg Leu Leu Glu Thr Val Glu Tyr Asn Ile Ser Gly
    1475            1480                1485

Ala Glu Arg Thr Ala His Ile Ser Gly Leu Pro Pro Ser Thr Asp
    1490            1495                1500

Phe Ile Val Tyr Leu Ser Gly Leu Ala Pro Ser Ile Arg Thr Lys
    1505            1510                1515

Thr Ile Ser Ala Thr Ala Thr Thr Glu Ala Leu Pro Leu Leu Glu
    1520            1525                1530

Asn Leu Thr Ile Ser Asp Ile Asn Pro Tyr Gly Phe Thr Val Ser
    1535            1540                1545

Trp Met Ala Ser Glu Asn Ala Phe Asp Ser Phe Leu Val Thr Val
    1550            1555                1560

Val Asp Ser Gly Lys Leu Leu Asp Pro Gln Glu Phe Thr Leu Ser
    1565            1570                1575

Gly Thr Gln Arg Lys Leu Glu Leu Arg Gly Leu Ile Thr Gly Ile

-continued

```
              1580              1585              1590
Gly Tyr Glu Val Met Val Ser Gly Phe Thr Gln Gly His Gln Thr
    1595              1600              1605
Lys Pro Leu Arg Ala Glu Ile Val Thr Glu Ala Glu Pro Glu Val
    1610              1615              1620
Asp Asn Leu Leu Val Ser Asp Ala Thr Pro Asp Gly Phe Arg Leu
    1625              1630              1635
Ser Trp Thr Ala Asp Glu Gly Val Phe Asp Asn Phe Val Leu Lys
    1640              1645              1650
Ile Arg Asp Thr Lys Lys Gln Ser Glu Pro Leu Glu Ile Thr Leu
    1655              1660              1665
Leu Ala Pro Glu Arg Thr Arg Asp Leu Thr Gly Leu Arg Glu Ala
    1670              1675              1680
Thr Glu Tyr Glu Ile Glu Leu Tyr Gly Ile Ser Lys Gly Arg Arg
    1685              1690              1695
Ser Gln Thr Val Ser Ala Ile Ala Thr Thr Ala Met Gly Ser Pro
    1700              1705              1710
Lys Glu Val Ile Phe Ser Asp Ile Thr Glu Asn Ser Ala Thr Val
    1715              1720              1725
Ser Trp Arg Ala Pro Thr Ala Gln Val Glu Ser Phe Arg Ile Thr
    1730              1735              1740
Tyr Val Pro Ile Thr Gly Gly Thr Pro Ser Met Val Thr Val Asp
    1745              1750              1755
Gly Thr Lys Thr Gln Thr Arg Leu Val Lys Leu Ile Pro Gly Val
    1760              1765              1770
Glu Tyr Leu Val Ser Ile Ile Ala Met Lys Gly Phe Glu Glu Ser
    1775              1780              1785
Glu Pro Val Ser Gly Ser Phe Thr Thr Ala Leu Asp Gly Pro Ser
    1790              1795              1800
Gly Leu Val Thr Ala Asn Ile Thr Asp Ser Glu Ala Leu Ala Arg
    1805              1810              1815
Trp Gln Pro Ala Ile Ala Thr Val Asp Ser Tyr Val Ile Ser Tyr
    1820              1825              1830
Thr Gly Glu Lys Val Pro Glu Ile Thr Arg Thr Val Ser Gly Asn
    1835              1840              1845
Thr Val Glu Tyr Ala Leu Thr Asp Leu Glu Pro Ala Thr Glu Tyr
    1850              1855              1860
Thr Leu Arg Ile Phe Ala Glu Lys Gly Pro Gln Lys Ser Ser Thr
    1865              1870              1875
Ile Thr Ala Lys Phe Thr Thr Asp Leu Asp Ser Pro Arg Asp Leu
    1880              1885              1890
Thr Ala Thr Glu Val Gln Ser Glu Thr Ala Leu Leu Thr Trp Arg
    1895              1900              1905
Pro Pro Arg Ala Ser Val Thr Gly Tyr Leu Leu Val Tyr Glu Ser
    1910              1915              1920
Val Asp Gly Thr Val Lys Glu Val Ile Val Gly Pro Asp Thr Thr
    1925              1930              1935
Ser Tyr Ser Leu Ala Asp Leu Ser Pro Ser Thr His Tyr Thr Ala
    1940              1945              1950
Lys Ile Gln Ala Leu Asn Gly Pro Leu Arg Ser Asn Met Ile Gln
    1955              1960              1965
Thr Ile Phe Thr Thr Ile Gly Leu Leu Tyr Pro Phe Pro Lys Asp
    1970              1975              1980
```

-continued

```
Cys Ser Gln Ala Met Leu Asn Gly Asp Thr Thr Ser Gly Leu Tyr
    1985                1990            1995

Thr Ile Tyr Leu Asn Gly Asp Lys Ala Gln Ala Leu Glu Val Phe
    2000                2005            2010

Cys Asp Met Thr Ser Asp Gly Gly Gly Trp Ile Val Phe Leu Arg
    2015                2020            2025

Arg Lys Asn Gly Arg Glu Asn Phe Tyr Gln Asn Trp Lys Ala Tyr
    2030                2035            2040

Ala Ala Gly Phe Gly Asp Arg Arg Glu Glu Phe Trp Leu Gly Leu
    2045                2050            2055

Asp Asn Leu Asn Lys Ile Thr Ala Gln Gly Gln Tyr Glu Leu Arg
    2060                2065            2070

Val Asp Leu Arg Asp His Gly Glu Thr Ala Phe Ala Val Tyr Asp
    2075                2080            2085

Lys Phe Ser Val Gly Asp Ala Lys Thr Arg Tyr Lys Leu Lys Val
    2090                2095            2100

Glu Gly Tyr Ser Gly Thr Ala Gly Asp Ser Met Ala Tyr His Asn
    2105                2110            2115

Gly Arg Ser Phe Ser Thr Phe Asp Lys Asp Thr Asp Ser Ala Ile
    2120                2125            2130

Thr Asn Cys Ala Leu Ser Tyr Lys Gly Ala Phe Trp Tyr Arg Asn
    2135                2140            2145

Cys His Arg Val Asn Leu Met Gly Arg Tyr Gly Asp Asn Asn His
    2150                2155            2160

Ser Gln Gly Val Asn Trp Phe His Trp Lys Gly His Glu His Ser
    2165                2170            2175

Ile Gln Phe Ala Glu Met Lys Leu Arg Pro Ser Asn Phe Arg Asn
    2180                2185            2190

Leu Glu Gly Arg Arg Lys Arg Ala
    2195                2200
```

METHOD FOR DIAGNOSING PULMONARY ARTERY HYPERTENSION

CROSS REFERENCE TO RELATED APPLICATIONS

Figure 1:
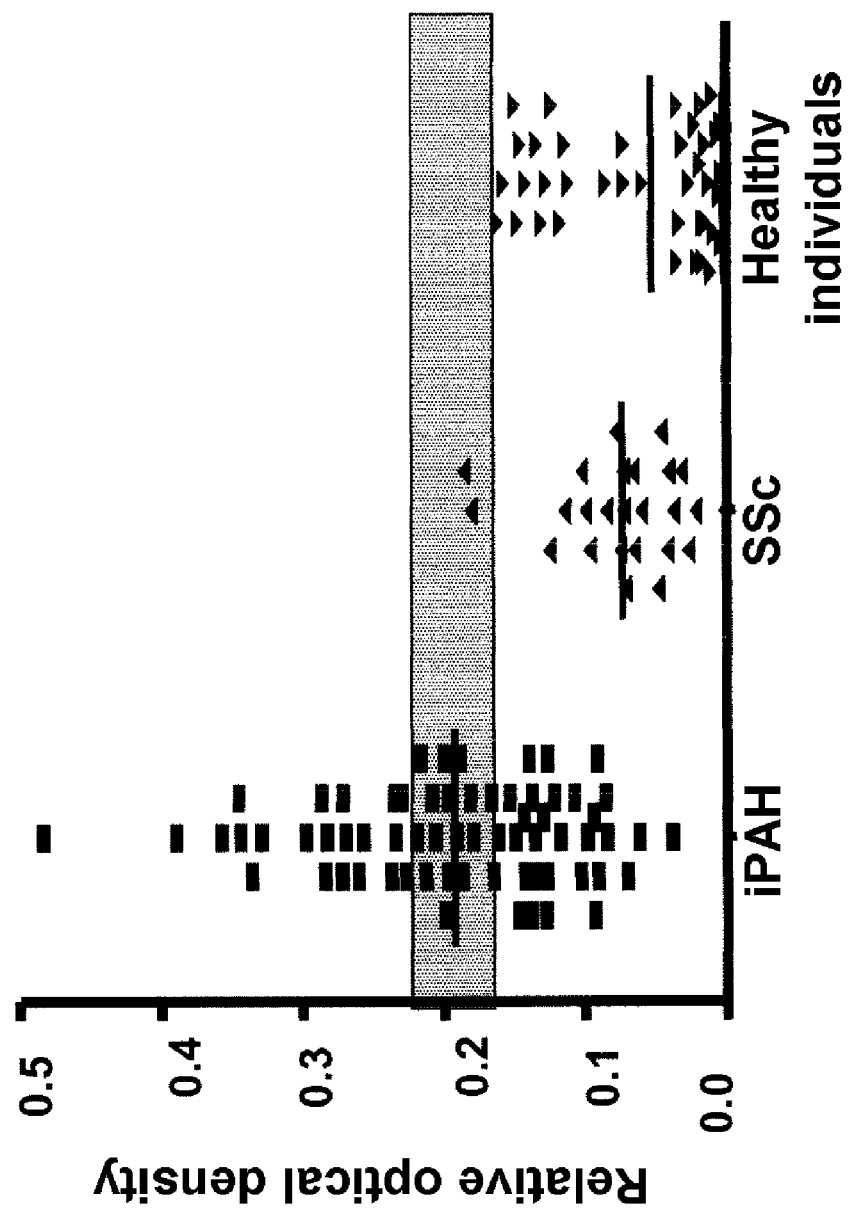

This application is a National Stage of International Application No. PCT/FR2009/050661, filed on Apr. 10, 2009, which claims the priority of French Application No. 0852459, filed on Apr. 11, 2008. The contents of the prior applications mentioned above are incorporated herein by reference in its entirety.

The invention relates to the diagnosing and the follow-up of pulmonary arterial hypertension.

PRIOR ART

Pulmonary arterial hypertension (PAH) is a rare pathological condition responsible for the occurrence of right cardiac decompensation which can result in death. PAH is defined by the demonstration, by right catheterization, of an average pulmonary arterial pressure of greater than or equal to 25 mmHg while resting or of greater than of equal to 30 mmHg while exercising, in the absence of elevated pulmonary capillary pressure (Rubin, 1997). The occurrence of PAH is the result of a chronic obstruction of the small pulmonary arteries secondary to the proliferation of endothelial cells, vascular smooth muscle cells and fibroblast (Dorfmuller et al., 2003). In particular, during severe PAH, a layer of myofibroblasts and of extracellular matrix forms which localizes between the endothelium and the internal elastic lamina, called neointima, which is characteristic of this condition. PAH can occur during the progression of pathological conditions with an autoimmune component, namely the connective tissue diseases, in particular systemic scleroderma (Hachulla et al., 2005), Sharp's syndrome and systemic lupus erythematosus. In addition, during idiopathic PAH, autoimmunity stigmata, namely anti-nuclear antibodies or anti-thyroglobulin antibodies, are from time to time found.

The presence of anti-endothelial cell antibodies (Tamby et al., 2005) and of anti-fibroblast antibodies (Tamby et al., 2006) has been reported during idiopathic PAH or PAH associated with systemic scleroderma. However, the predictive value of these antibodies in terms of the occurrence of PAH has not been studied and the potential role of autoimmune phenomena in idiopathic PAH pathogenicity remains uncertain (Mouthon et al., 2005).

In most cases, PAH is screened for when the patient presents stage III or IV dyspnea. When the patient is monitored for a chronic disease such as systemic scleroderma, PAH is screened for by annual echocardiography.

However, a simple and reliable test to screen for PAH is still lacking, and would be invaluable for the earliest possible diagnosis, which would make it possible to rapidly set up therapeutic strategies for improving the condition of the patient and the survival chances for said patient.

SUMMARY OF THE INVENTION

The invention now provides an in vitro method for detecting PAH, or a risk of developing PAH, which comprises determining the presence and/or the amount of anti-tenascin C (TN-C) antibodies in a biological sample originating from a patient, the presence of anti-TN-C antibodies being indicative of PAH or of a risk of developing PAH.

Preferably, the presence of anti-tenascin C antibodies in the biological sample is compared with a control value, the presence of anti-tenascin C antibodies in an amount greater than the control value being indicative of PAH or of a risk of developing PAH.

Another subject of the invention is an in vitro method for the prognosis or follow-up of PAH, which comprises determining the presence and/or the amount of anti-TN-C antibodies in a biological sample originating from a patient, at various times, an increase in the amount of anti-TN-C antibodies over time being indicative of a worsening of the PAH.

Another subject of the invention is an in vitro method for evaluating the efficacy of a treatment for PAH, which comprises determining the presence and/or the amount of anti-TN-C antibodies in a biological sample originating from a patient, at various times before, during or after the treatment, a decrease in the amount of anti-TN-C antibodies over time being indicative of an improvement in the PAH.

DETAILED DESCRIPTION OF THE INVENTION

TN-C is expressed inside and around the blood vessels in the fetal lung (Rettig et al., 1994), but it is no longer subsequently expressed in normal adult pulmonary arteries (Jones et al., 1996). Moreover, the loss of signaling via BMPRII, responsible for a lack of regulatory T cells that can predispose to the occurrence of PAH (Nicolls et al., 2005), can also induce the expression of TN-C in vivo and on vascular cells in culture (Ihida-Stansbury et al., 2006). On this basis, the inventors put forward the hypothesis that patients who have PAH could develop an immune response directed against TN-C. Thus, they decided to search for anti-TN-C antibodies in the serum of patients suffering from PAH.

The inventors were thus able to demonstrate a correlation between the occurrence of PAH and the production of anti-TN-C antibodies. On this basis, they propose an in vitro method for the diagnosis or the prognosis of PAH, or of a risk of developing PAH, which comprises determining the presence and/or the amount of anti-TN-C antibodies in a biological sample originating from a patient. The anti-TN-C antibodies detected are preferably immunoglobulins G (IgGs).

DEFINITIONS

Tenascin C (or TN-C) is an extracellular matrix glycoprotein. It is also known as hexabrachion or cytotactin. A human TN-C sequence is reported in the annex (SEQ ID No. 1).

The term "biological sample" refers to any biological sample originating from a patient. Examples of samples include biological fluids and tissue biopsies. Preferably, the sample may be blood, serum, saliva, urine or sperm. More preferably, the biological sample is a blood or serum sample.

The term "patient" refers to any individual capable of being tested. Preferably, it is a human being, but the term includes any other mammal, such as dogs, cats, rodents, cattle, horses, monkeys, etc. The patient can be tested irrespective of the sex or age thereof. The patient may be an individual at risk, may be asymptomatic, or may show early or advanced signs of PAH. For example, the patient may be an individual predisposed to developing PAH, in particular an individual carrying one or more mutations in the gene encoding BMPRII.

The term "diagnosis" means the identification of the pathological condition or the evaluation of the state of severity of the pathological condition.

The term "prognosis" means the evaluation of the risk of worsening, and of the consequences thereof.

The term "control value" refers to a basal value corresponding to the average of the values obtained with the biological sample from healthy individuals, not suffering from PAH or a disease capable of leading to PAH. It may be a statistical reference value.

In order to evaluate the progression of the pathological condition, it may be useful to test a patient and to verify the effect of a treatment or the progression of the pathological condition by testing the patient again, for example with a gap of several months. In this case, the results of the second test are compared with the results of the first test, and also often with the "control" value.

An amount of anti-TN-C antibodies "greater than the control value" generally means a statistically significant increase, for example of at least two standards deviations above the mean of the optical densities of the IgG reactivities of all the healthy individuals.

The "capture antigen" is intended to mean an antigen, preferably attached to a solid phase, which is capable of retaining the anti-TN-C antibody present in a biological sample, by affinity binding. The capture antigen can be labeled.

The term "labeled" refers both to a direct labeling (by means of enzymes, radioisotopes, fluorochromes, luminescent compounds, etc.) and an indirect labeling (for example by means of antibodies which are themselves directly labeled or using reagents of a labeled "affinity pair", such as, but not exclusively, the labeled avidin-biotin pair, etc.).

Assaying of Antibodies

The biological sample is preferably a serum sample, diluted to 1/100th, or more, for example to 1/200th or 1/400th.

Advantageously, the amount of anti-TN-C antibody can be determined by an immunoassay.

The biological sample can be optionally treated in a prior step, or brought directly into contact with at least one capture antigen.

The method according to the invention can be carried out according to various formats well known to those skilled in the art: in solid phase or in homogenous phase; in one step or in two steps; in a competition method, by way of nonlimiting examples.

According to one preferred embodiment, the capture antigen is immobilized on a solid phase. By way of nonlimiting examples of a solid phase, use may be made of microplates, in particular polystyrene microplates, such as those sold by the company Nunc, Denmark. Use may also be made of solid particles or beads, paramagnetic beads, such as those provided by Dynal or Merck-Eurolab (France) (under the trademark Estapor™), or else polystyrene or polypropylene test tubes, etc.

An immunoassay format for detecting antibodies by competition is also possible. Other immunoassay modes can also be envisioned and are well known to those skilled in the art.

ELISA assays, radioimmunoassays, or any other detection technique can be used for revealing the presence of the antigen-antibody complexes formed.

According to one preferred embodiment, the method of the invention comprises bringing a biological sample into contact with a protein comprising the fragment of amino acids 181 to 290 of the human TN-C sequence as represented in SEQ ID No. 1.

In one particular example, the capture antigen, which can be a protein comprising the fragment of amino acids 181 to 290 of the human TN-C sequence, can be coupled to a glutathione S transferase (GST), before being deposited on a microplate.

Serum samples to be tested, prediluted to 1/100th, are incubated on the microplate. After washing, labeled anti-human Fcγ antibodies (for example, labeled with an alkaline phosphatase) are added, the complexes being revealed, for example, by addition of a substrate for the phosphatase, the cleavage of which can be detected by reading the absorbance.

Patients Targeted

The patients targeted are those who may develop PAH.

This may involve a patient who suffers from a connective tissue disease, such as systemic scleroderma, Sharp's syndrome (which is a mixed connective tissue disease) or systemic lupus erythematosus.

The patient may also be suffering from idiopathic or familial PAH.

More generally, any patient suffering from a pulmonary vascular disease can be advantageously subjected to the method for detecting PAH as defined in the invention.

Moreover, the PAH detected may also be portopulmonary hypertension (i.e. PAH associated with portal hypertension), or be associated with a congenital heart disease, or with a human immunodeficiency virus (HIV) infection, or else be post-embolic pulmonary hypertension, complicating the progression of a chronic obstructive bronchitis or of cyanogenic heart disease.

Other patients targeted are those exposed to certain appetite-suppressing drugs, such as fenfluramine, the prescription of which can contribute to the occurrence of PAH.

Other individuals capable of benefiting from this type of test are those carrying a mutation in the gene encoding BMPRII and who, optionally, do not present PAH detectable by echography, so as to screen for individuals who may subsequently develop PAH.

Evaluation of the Efficacy of a Treatment

Another subject of the invention is an in vitro method for evaluating the efficacy of a treatment for PAH, which comprises determining the presence and/or the amount of anti-TN-C antibodies in a biological sample originating from a patient, at various times before, during or after the treatment, a decrease in the amount of anti-TN-C antibodies over time being indicative of an improvement in the PAH.

The current conventional treatment for PAH combines symptomatic treatment and a vasodilator treatment. The symptomatic treatment combines anti-coagulants, oxygen therapy and diuretics. The vasodilator treatment is based on the following molecules: calcium channel blockers, epoprostenol (prostacyclin) prescribed intravenously as a continuous infusion, selective or nonselective endothelin receptor inhibitors, in particular bosentan, sytaxentan and ambrysentan, phosphodiesterase type 5 inhibitors, in particular sildenafil, all these medicaments being administered orally, and inhaled iloprost, a prostacyclin analog which is administered by inhalation. These treatments can be optionally combined. In the event of these therapies failing, a lung or heart-lung transplant can be proposed.

The following figures and examples illustrate the invention without limiting the scope thereof.

FIGURE LEGEND

FIG. 1 is a graph showing the detection of anti-TN-C antibodies by ELISA assay. The serum IgGs from the patients suffering from idiopathic PAH, from the patients suffering from systemic scleroderma and from the healthy individuals paired for sex and age were tested with respect to a recombinant TN-C fragment, at a dilution of 1/100th. The lower and upper limits of the dotted zone represent the thresholds defined by two and three times the standard deviation above the mean of the optical densities obtained in the healthy patients. The significant differences between the groups of patients and the healthy individuals are estimated using a Mann-Whitney rank test and are indicated by:

*: p<0.01
**: p<0.001.

Figure 2:
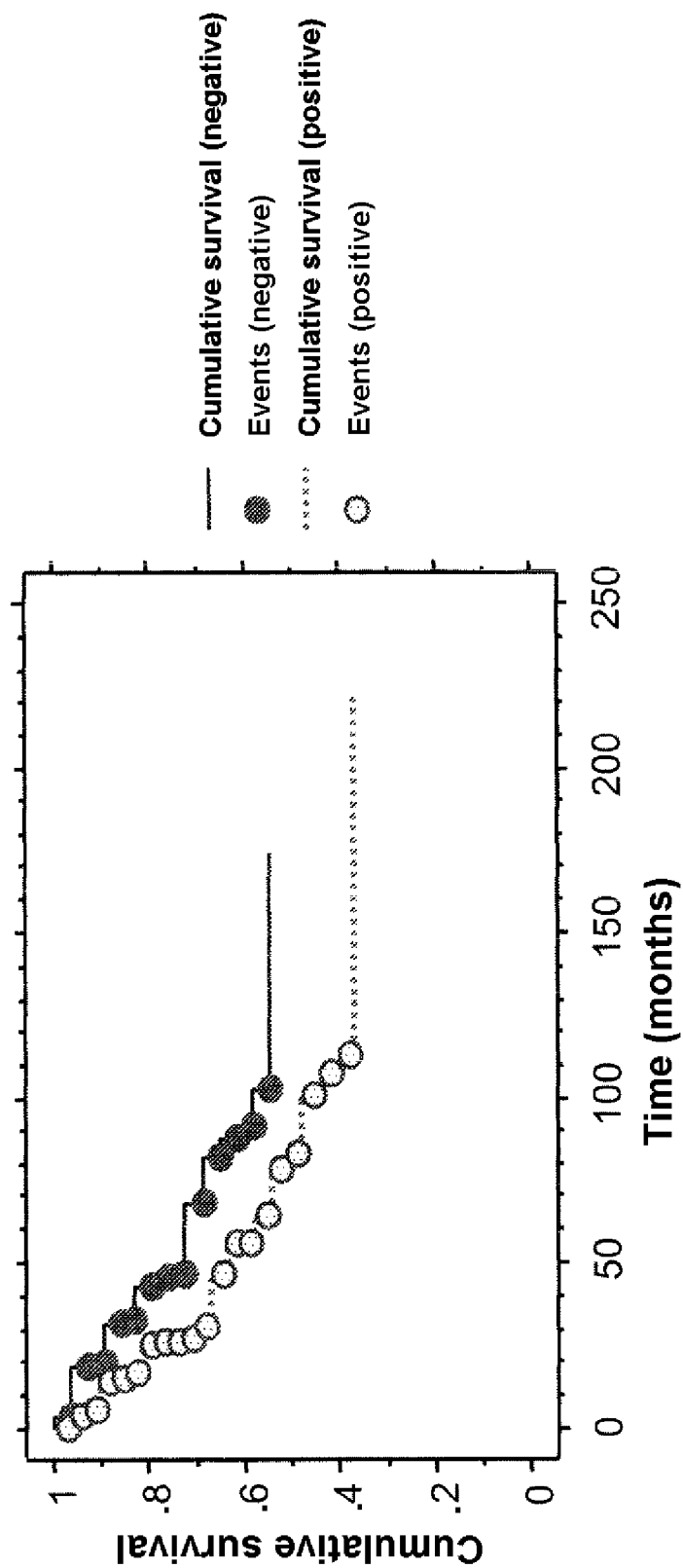

FIG. 2 represents survival curves according to Kaplan and Meier as a function of the presence or the absence of anti-TN-C antibodies. Along the X-axis, the time in months; along the Y-axis, the percentage cumulative survival.

EXAMPLE

Detection of Anti-Tenascin C Antibodies in Patients Suffering From Pulmonary Arterial Hypertension Materials and Methods
Patients PAH was screened for by demonstrating, through transthoracic echocardiography, a systolic pulmonary arterial pressure of greater than 40 mmHg. In all cases, the PAH was confirmed by performing a right catheterization and demonstrating an average pulmonary arterial pressure of greater than or equal to 25 mmHg at rest and greater than or equal to 30 mmHg with physical exercise. By convention, the PAH was described as idiopathic if the patient showed no associated pathological condition, it then being possible for the PAH to correspond to sporadic PAH, familial PAH or PAH associated with exposure to fenfluramine 91 patients were included in the study comprising 66 (72.5%) patients having idiopathic PAH (IPAH) and 25 patients having systemic scleroderma corresponding to the criteria of the American College of Rheumatology (ACR) and/or to the criteria of LeRoy and Medsger (Masi et al., 1980; LeRoy et al., 2001).

All the patients who had diffuse systemic scleroderma without PAH had pulmonary interstitial involvement demonstrated by a high-resolution thoracic scan and a vital capacity of less than 80% of the predicted value and/or a carbon monoxide transfer coefficient (DLCO) of less than 75% of the predicted value. None of the patients were receiving corticoid steroids or immunosuppressants at the time the samples were taken, and none of them had a solid tumor or another associated connective tissue disease. 46 healthy individuals paired for sex and age were used as controls.

ELISA Assay

The tenascin C (TN-C) was obtained from the company Abnova (Abnova Corporation, Taipei city, Taiwan). The antigen used consisted of the fragment 181 to 290 of TN-C (SEQ ID No. 1), coupled to a GST unit. The TN-C was diluted in a bicarbonate buffer and deposited onto 96-well plates (Maxisorb, NalgeNunc Int. Rochester, N.Y., USA) at a final concentration of 4 µg/ml at 4° C. The sera from patients and from healthy individuals were diluted to ¹⁄₁₀₀th in a phosphate buffer (PBS) containing 1% albumin, and incubated for one hour at 37° C. After washing, alkaline phosphatase-conjugated rabbit anti-human Fcγ antibodies (Dakocytomation, Golstrup, Denmark) were added and incubated for one hour at ambient temperature. The reactivities were revealed by adding 0.05M p-nitrophenylphosphate in a magnesium carbonate buffer (pH 9.8) and the absorbance at 405 nm was determined using an ELISA plate reader (Fusion, Packard BioScience, Meriden, Conn., USA). In order to take into account the variability between wells, the optical density of a reference serum was arbitrarily defined as 100% of the anti-TN-C activity. The results of the samples tested were calculated from the mean of the absorbance of duplicate wells and expressed as a percentage of this reference value. All the samples were tested in duplicate.

Statistical Analyses

All the statistical analyses were carried out using the Systat software (version 11.0 Systat Software Inc, Point Richmond, Calif., USA). A Mann-Whitney test was used to compare the relative optical densities of the various groups. P values of less than 0.05 were considered to be statistically significant. The survival was calculated by the Kaplan and Meier method (Kaplan and Meier, 1958).

Results

The reactivities of the IgGs of the patients suffering from idiopathic PAH, of the patients suffering from systemic scleroderma with or without PAH and of the control individuals, with respect to TN-C, were studied by ELISA. Using a threshold defined by two standard deviations above the mean of the optical densities of the IgG reactivities of all the healthy individuals, 36/66 (54.5%) of the patients with idiopathic PAH and 2/25 (8%) of the scleroderma patients had anti-TN-C IgGs. None of the healthy individuals had anti-TN-C IgGs (FIG. 1). When the threshold was shifted to three standard deviations above the mean of the IgG reactivities of the healthy individuals, 12/66 (18.1%) of the patients with idiopathic PAH had anti-TN-C IgGs and no scleroderma patient had anti-TN-C IgGs. The reactivities of the anti-TN-C antibody serum IgGs of patients with idiopathic PAH were significantly higher than those of the scleroderma patients (p<0.001), and than those of the healthy individuals (p<0.001). Similarly, the reactivities of the anti-TN-C antibody serum IgGs of scleroderma patients were significantly higher than those of the healthy individuals (p=0.021) (FIG. 1).

No significant difference in the clinical presentation and the data from the echocardiography, from the right catheterization and from the 6 minute walking test was demonstrated between the two groups of patients. Survival was decreased in the group of patients having anti-TN-C antibodies compared with the patients whose did not have anti-TN-C antibodies, without, however, this difference being significant in this case (p=0.17).

The appearance of an immune response directed against TN-C could result from the same mechanisms as those that result in the induction of TN-C expression and in the proliferation of smooth muscle cells. The presence of anti-TN-C antibodies would therefore be correlated with the appearance of vascular remodeling, constituting a marker for the occurrence of PAH.

LITERATURE REFERENCES

Dorfmuller et al., 2003, Eur Respir J, 22(2):358-63
Hachulla et al., 2005, Arthritis Rheum 52(12):3792-3800
Ihida-Stansbury et al., 2006, Am J Physiol Lung Cell Mol Physiol 291(4):L694-702
Jones et al., 1996, Circ Res 79(6):1131-42
Kaplan and Meier, 1958, J Am Stat Assoc 53:457-81
LeRoy et al., 2001, J Rheumatol 28(7):1573-76
Masi et al., 1980, Arthr Rheum 23:581-90
Mouthon et al., 2005, Eur Respir J 26(6):986-8
Nicolls et al., 2005, Eur Respir J 26(6):1110-8
Rettig et al., 1994, J Cell Sci; 107 (Pt 2):487-97
Rubin, 1997, N Engl J Med, 336(2):111-7
Tamby et al., 2005, Thorax 60(9):765-72
Tamby et al., 2006, Eur Respir J 28(4):799-807

The invention claimed is:

1. An in vitro method for determining a likelihood for a patient to have or to develop pulmonary arterial hypertension (PAH), the method comprising determining by an immunoassay an amount of anti-tenascin C antibodies binding to an epitope in a protein fragment consisting of amino acids 181 to 290 of SEQ ID NO:1, in a serum, blood, or plasma sample originating from a patient and comparing the amount to a control value, wherein the amount of anti-tenascin C antibodies in the sample being greater than the control value indicates that the patient likely has PAH or is at risk of developing PAH.

2. The method as claimed in claim 1, in which the immunoassay is an enzyme-linked immunosorbent assay.

3. The method as claimed in claim 1, in which the patient is a human being.

4. The method as claimed in claim 1, in which the patient suffers from systemic scleroderma.

5. The method as claimed in claim 1, in which the patient suffers from Sharp's syndrome.

6. The method as claimed in claim 1, in which the patient suffers from systemic lupus erythematosus.

7. The method as claimed in claim 1, in which the patient suffers from idiopathic PAH.

8. The method as claimed in claim 1, in which the PAH is associated with portal hypertension, with congenital heart disease, or with a human immunodeficiency virus infection, or is post-embolic pulmonary hypertension.

9. The method as claimed in claim 1, in which the patient is an individual predisposed to developing PAH.

10. The method as claimed in claim 9, in which the individual carries one or more mutation(s) in a gene encoding bone morphogenetic protein receptor II.

* * * * *

UNITED STATES PATENT AND TRADEMARK OFFICE
CERTIFICATE OF CORRECTION

PATENT NO. : 8,609,356 B2 Page 1 of 1
APPLICATION NO. : 12/936745
DATED : December 17, 2013
INVENTOR(S) : Mouthon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this
Twenty-second Day of September, 2015

Michelle K. Lee
*Director of the United States Patent and Trademark Office*